United States Patent
Lee et al.

(10) Patent No.: US 11,173,132 B2
(45) Date of Patent: Nov. 16, 2021

(54) TRANSDERMAL ADHESIVE COMPOSITION COMPRISING A VOLATILE LIQUID THERAPEUTIC AGENT HAVING LOW MELTING POINT

(71) Applicant: Corium, Inc., Menlo Park, CA (US)

(72) Inventors: Eun Soo Lee, Redwood City, CA (US); Parminder Singh, Union City, CA (US); Appala Sagi, Mountain View, CA (US); Amit K. Jain, Milpitas, CA (US)

(73) Assignee: Corium, Inc., Grand Rapids, MI (US)

( * ) Notice: Subject to any disclaimer, the term of this patent is extended or adjusted under 35 U.S.C. 154(b) by 84 days.

(21) Appl. No.: 16/228,641

(22) Filed: Dec. 20, 2018

(65) Prior Publication Data
US 2019/0183810 A1    Jun. 20, 2019

Related U.S. Application Data

(60) Provisional application No. 62/608,460, filed on Dec. 20, 2017.

(51) Int. Cl.
| | |
|---|---|
| *A61K 9/70* | (2006.01) |
| *A61P 25/28* | (2006.01) |
| *A61K 47/12* | (2006.01) |
| *A61K 31/13* | (2006.01) |
| *A61K 9/00* | (2006.01) |

(52) U.S. Cl.
CPC .......... *A61K 9/7061* (2013.01); *A61K 9/0014* (2013.01); *A61K 9/7069* (2013.01); *A61K 31/13* (2013.01); *A61K 47/12* (2013.01); *A61P 25/28* (2018.01)

(58) Field of Classification Search
None
See application file for complete search history.

(56) References Cited

U.S. PATENT DOCUMENTS

| | | |
|---|---|---|
| 3,391,142 A | 7/1968 | Mills et al. |
| 3,546,141 A | 12/1970 | Washburn et al. |
| 3,549,016 A | 12/1970 | Rigopulos |
| 4,122,193 A | 10/1978 | Scherm et al. |
| 4,273,774 A | 6/1981 | Scherm |
| 4,781,924 A | 11/1988 | Lee et al. |
| 4,837,027 A | 6/1989 | Lee et al. |
| 4,849,224 A | 7/1989 | Chang et al. |
| 4,880,633 A | 11/1989 | Loper et al. |
| 4,886,812 A | 12/1989 | Griss et al. |
| 4,895,841 A | 1/1990 | Sugimoto et al. |

(Continued)

FOREIGN PATENT DOCUMENTS

| | | |
|---|---|---|
| CA | 2332012 A1 | 11/1999 |
| CN | 1174031 A | 2/1998 |

(Continued)

OTHER PUBLICATIONS

US 9,095,635 B1, 08/2015, Willmann et al. (withdrawn)

(Continued)

*Primary Examiner* — Isis A Ghali
(74) *Attorney, Agent, or Firm* — McDermott Will & Emery LLP; Judy M. Mohr; Brennen P. Baylor

(57) ABSTRACT

Methods, compositions, and devices for transdermally administering an active agent such as memantine are provided.

10 Claims, 2 Drawing Sheets

(56) References Cited

U.S. PATENT DOCUMENTS

| | | |
|---|---|---|
| 5,026,556 A | 6/1991 | Drust et al. |
| 5,061,703 A | 10/1991 | Bormann et al. |
| 5,123,900 A | 6/1992 | Wick |
| 5,132,115 A | 7/1992 | Wolter et al. |
| 5,252,588 A | 10/1993 | Azuma et al. |
| 5,296,512 A | 3/1994 | Beier et al. |
| 5,424,077 A | 6/1995 | Lajoie |
| 5,614,560 A | 3/1997 | Lipton |
| 5,635,203 A | 6/1997 | Gale et al. |
| 5,662,925 A | 9/1997 | Ebert et al. |
| 5,730,999 A | 3/1998 | Lehmann et al. |
| 5,866,585 A | 2/1999 | Fogel |
| 5,958,919 A | 9/1999 | Olney et al. |
| 6,004,578 A | 12/1999 | Lee et al. |
| 6,255,348 B1 | 7/2001 | Elstner |
| 6,383,471 B1 | 5/2002 | Chen et al. |
| 6,512,010 B1 | 1/2003 | Gale et al. |
| 6,521,639 B1 | 2/2003 | Murahashi et al. |
| 6,746,689 B2 | 6/2004 | Fischer et al. |
| 6,923,988 B2 | 8/2005 | Patel et al. |
| 6,929,801 B2 | 8/2005 | Klose et al. |
| 7,097,853 B1 | 8/2006 | Garbe et al. |
| 7,176,185 B2 | 2/2007 | Hilfinger et al. |
| 7,250,394 B2 | 7/2007 | Nedergaard |
| 7,320,802 B2 | 1/2008 | Ryde et al. |
| 7,335,379 B2 | 2/2008 | Carrara et al. |
| 7,462,743 B2 | 12/2008 | Merli et al. |
| 7,670,838 B2 | 3/2010 | Deisseroth et al. |
| 7,682,628 B2 | 3/2010 | Singh |
| 7,744,918 B2 | 6/2010 | Yamaguchi et al. |
| 7,858,114 B2 | 12/2010 | Ito |
| 7,888,422 B2 | 2/2011 | Jackson et al. |
| 8,058,291 B2 | 11/2011 | Went et al. |
| 8,168,209 B2 | 5/2012 | Went et al. |
| 8,246,978 B2 | 8/2012 | Kydonieus et al. |
| 8,252,321 B2 | 8/2012 | Dipierro et al. |
| 8,283,379 B2 | 10/2012 | Went et al. |
| 8,362,085 B2 | 1/2013 | Went et al. |
| 8,512,742 B2 | 8/2013 | Amano et al. |
| 8,614,274 B2 | 12/2013 | Jackson et al. |
| 8,673,338 B2 | 3/2014 | Bleier |
| 8,784,879 B2 | 7/2014 | Singh et al. |
| 8,815,281 B2 | 8/2014 | Kanios et al. |
| 8,840,922 B2 | 9/2014 | Kawakami et al. |
| 8,840,935 B2 | 9/2014 | Haber et al. |
| 8,874,879 B2 | 10/2014 | Ge et al. |
| 9,012,511 B2 | 4/2015 | Neville et al. |
| 9,248,104 B2 | 2/2016 | Valia et al. |
| 9,622,986 B2 | 4/2017 | Im et al. |
| 9,993,466 B2 | 6/2018 | Lee et al. |
| 10,016,372 B2 | 7/2018 | Singh et al. |
| 10,300,025 B2 | 5/2019 | Lee et al. |
| 10,307,379 B2 | 6/2019 | Lee et al. |
| 2001/0031787 A1 | 10/2001 | Hsu et al. |
| 2002/0192243 A1 | 12/2002 | Hsu et al. |
| 2003/0170308 A1 | 9/2003 | Cleary et al. |
| 2004/0018241 A1 | 1/2004 | Houze et al. |
| 2004/0022835 A1 | 2/2004 | Pai et al. |
| 2004/0033254 A1 | 2/2004 | Song et al. |
| 2004/0087658 A1 | 5/2004 | Moebius |
| 2005/0113458 A1 | 5/2005 | Gupta et al. |
| 2006/0035888 A1* | 2/2006 | Jonas .................... A61K 31/13 514/220 |
| 2006/0205822 A1 | 9/2006 | Jonas et al. |
| 2008/0038328 A1 | 2/2008 | Higo et al. |
| 2008/0107719 A1 | 5/2008 | Likitlersuang et al. |
| 2008/0131490 A1 | 6/2008 | Hanatani et al. |
| 2008/0131491 A1 | 6/2008 | Hanatani et al. |
| 2008/0138388 A1 | 6/2008 | Aida et al. |
| 2009/0081259 A1 | 3/2009 | Jonas et al. |
| 2009/0124659 A1 | 5/2009 | Moebius |
| 2009/0156639 A1 | 6/2009 | Trippodi-Murphy et al. |
| 2009/0175929 A1 | 7/2009 | Terahara et al. |
| 2009/0291127 A1 | 11/2009 | Wen et al. |
| 2010/0121290 A1 | 5/2010 | Rasmussen et al. |
| 2010/0178037 A1 | 7/2010 | Chen et al. |
| 2010/0227852 A1 | 9/2010 | Moebius |
| 2010/0291186 A1 | 11/2010 | Singh et al. |
| 2011/0059141 A1 | 3/2011 | Ito |
| 2011/0059169 A1 | 3/2011 | Went et al. |
| 2011/0066120 A1* | 3/2011 | Lee .................... A61F 13/0246 604/290 |
| 2011/0244023 A1 | 10/2011 | Cottrell et al. |
| 2011/0313372 A1* | 12/2011 | Eifler .................... A61K 31/13 604/304 |
| 2012/0121729 A1 | 5/2012 | Paterson et al. |
| 2012/0245537 A1 | 9/2012 | Horstmann et al. |
| 2013/0053358 A1 | 2/2013 | Aida et al. |
| 2013/0331803 A1 | 12/2013 | Fleschhut et al. |
| 2014/0052081 A1 | 2/2014 | Yang et al. |
| 2014/0148456 A1 | 5/2014 | Likitlersuang et al. |
| 2014/0256690 A1 | 9/2014 | Arkady et al. |
| 2014/0322284 A1 | 10/2014 | Singh et al. |
| 2014/0370076 A1 | 12/2014 | Choi et al. |
| 2015/0098980 A1 | 4/2015 | Pongpeerapat et al. |
| 2016/0051486 A1 | 2/2016 | Choi et al. |
| 2017/0202830 A1 | 7/2017 | Stinchcomb et al. |
| 2017/0360908 A1 | 12/2017 | Shishido et al. |
| 2018/0028461 A1 | 2/2018 | Singh et al. |
| 2018/0028462 A1 | 2/2018 | Lee et al. |
| 2018/0028463 A1 | 2/2018 | Lee et al. |
| 2018/0028466 A1 | 2/2018 | Lee et al. |
| 2018/0028467 A1 | 2/2018 | Singh et al. |
| 2018/0028512 A1 | 2/2018 | Lee et al. |
| 2018/0028663 A1 | 2/2018 | Lee et al. |
| 2018/0185298 A1 | 7/2018 | Jain et al. |
| 2018/0235901 A1 | 8/2018 | Lee et al. |
| 2019/0029971 A1 | 1/2019 | Lee et al. |

FOREIGN PATENT DOCUMENTS

| | | |
|---|---|---|
| CN | 1895242 B | 1/2007 |
| CN | 102048678 A | 5/2011 |
| CN | 105693556 A | 6/2016 |
| EP | 0296560 A2 | 12/1988 |
| EP | 0540623 B1 | 9/1994 |
| EP | 1423100 A1 | 6/2004 |
| EP | 1682109 B1 | 10/2008 |
| EP | 2016941 A1 | 1/2009 |
| EP | 2090310 A1 | 8/2009 |
| EP | 2098233 A1 | 9/2009 |
| EP | 2098235 A1 | 9/2009 |
| EP | 2260839 A2 | 12/2010 |
| EP | 2514415 A1 | 10/2012 |
| EP | 2638906 A1 | 9/2013 |
| EP | 2818161 A1 | 12/2014 |
| JP | H06-199659 A | 7/1994 |
| JP | 2009-013171 A | 1/2009 |
| JP | 2009-203213 A | 9/2009 |
| JP | 2015-151370 A | 8/2015 |
| KR | 2009-0101667 A | 9/2009 |
| WO | WO 1996/019205 A1 | 6/1996 |
| WO | WO 1996/040087 A2 | 12/1996 |
| WO | WO 2003/020248 A1 | 3/2003 |
| WO | WO 2003/055471 A1 | 7/2003 |
| WO | WO 2005/079779 A1 | 9/2005 |
| WO | WO 2007/129427 A1 | 11/2007 |
| WO | WO 2008/021113 A2 | 2/2008 |
| WO | WO 2010/051349 A1 | 5/2010 |
| WO | WO 2011/070361 A1 | 6/2011 |
| WO | WO 2011/081628 A1 | 7/2011 |
| WO | WO 2012/084969 A1 | 6/2012 |
| WO | WO 2012/089256 A1 | 7/2012 |
| WO | WO 2012/097197 A1 | 7/2012 |
| WO | WO 2014/174564 A1 | 10/2014 |
| WO | WO 2015/053878 A1 | 4/2015 |
| WO | WO 2015/200472 A1 | 12/2015 |
| WO | WO 2016/046675 A1 | 3/2016 |
| WO | WO 2016/099198 A1 | 6/2016 |
| WO | WO 2016/209982 A1 | 12/2016 |
| WO | WO 2017/018321 A1 | 2/2017 |
| WO | WO 2017/117554 A1 | 7/2017 |
| WO | WO 2017/223402 A1 | 12/2017 |
| WO | WO 2018/022814 A1 | 2/2018 |

(56) References Cited

FOREIGN PATENT DOCUMENTS

| WO | WO 2018/022815 A1 | 2/2018 |
|---|---|---|
| WO | WO 2018/022816 A1 | 2/2018 |
| WO | WO 2018/022817 A1 | 2/2018 |
| WO | WO 2018/022818 A1 | 2/2018 |

OTHER PUBLICATIONS

Cabot Corporation, "Fumed Metal Oxides". 5 pages, Retreived from the internet on May 13, 2019 from http://www.cabotcorp.com/solutions/products-plus/fumed-metl-oxides (2019).
Del Rio-Sancho et al., "Transdermal therapeutic systems for memantine delivery. Comparison of passive and iontophoretic transport", Int. J. Pharm., vol. 517, No. 1-2, pp. 104-111 (2017).
International Search Report from International Patent Application No. PCT/US2018/066848, 7 pages, dated Apr. 15, 2019.
Mittapelly et al., "In Depth Analysis of Pressure-Sensitive Adhesive Patch-Assisted Delivery of Memantine and Donepezil Using Physiologically Based Pharmacokinetic Modeling and in Vitro/in Vivo Correlations", Mol. Pharm., vol. 15, No. 7, pp. 2646-2655 (2018).
Shivalingam et al., "Formulation and evaluation of diclofenac potassium transdermal patches for enhanced therapeutic efficacy", Indian J. Res. Pharm. Biotechnol., pp. 1152-1157 (2014).
The Tamilnadu, "Formulation and evaluation of matrix type transdermal patched of benazepril hydrochloride", Dissertation submitted by R. Revathi, Reg. No. 26108606, to the Controller of Examination, Department of Pharmaceutics College of Pharmacy, Madurai Medical College, Madurai, 202 pages (2012).
Aida et al., "Adhesive patch useful in pharmaceuticals, for delivering drugs, provides single surface of support with adhesive layer, where adhesive layer contains drug in solution stae and crystalline state", Database WPI, AN 2008-F37689 (2013).
Ashall, "Tobacco Facts #4: Smokers are freebasing nicotine!—The Great Tobacco Plague", Dr Frank Ashalls Blog, Retreived from the Internet: https://biochemdr1.wordpress.com/2013/11/30/tobacco-fact-4-somkers-are-freebasing-nicotine/, 7 pages (Nov. 30, 2013).
Brantseva et al., "Rheological and adhesive properties of PIB-based pressure-sensitive adhesives with montmorillonite-type nanofillers", European Polymer Journal, vol. 76, pp. 228-244 (2016).
Chladek et al., "Steady-state bioequivalence studies of two memantine tablet and oral solution formulations in healthy volunteers", J. Appl. Biomed., vol. 6, pp. 39-45 (2008).
Choi et al., "Effect of fatty acids on the transdermal delivery of donepezil: in vitro and in vivo evaluation", Int. J. Pharm., vol. 422, No. 1-2, pp. 83-90 (2012).
Del Rio-Sancho, "Transdermal absorption of memantin—effect of chemical enhancers, iontophoresis, and role of enhancer lipophilicity", Eur J. Pharm. Biopharm., vol. 82, No. 1, pp. 164-170 (2012).
Fang et al., "Donepezil percutaneous absorption enhancer and back lining layer which includes polyethylene, polyester and ethylene-vinyl acetate copolymer", Database WPI, AN 2013-G75464 (2013).
Forchetti, "Treating patients with moderate to severe Alzheimer's disease: implications of recent pharmacologic studies", Prim. Care Companion J. Clin. Psychiatry., vol. 7, No. 4, pp. 155-161 (2005).
Fornasari et al., "Synthesis and antioxidant properties of novel memantine derivatives", Cent. Nerv. Syst. Agents Med. Chem., vol. 17, No. 2, pp. 123-128 (2017).
International Search Report from International Application No. PCT/US2016/038792 dated Sep. 27, 2016.
International Search Report from International Patent Application No. PCT/US2017/038934 dated Oct. 10, 2017.
International Search Report from International Patent Application No. PCT/US2017/044047 dated Nov. 3, 2017.
International Search Report from International Patent Application No. PCT/US2017/044048 dated Nov. 3, 2017.
International Search Report from International Patent Application No. PCT/US2017/044049 dated Nov. 7, 2017.
International Search Report from International Patent Application No. PCT/US2017/044050 dated Nov. 6, 2017.
International Search Report from International Patent Application No. PCT/US2017/044051 dated Nov. 2, 2017.
International Search Report from International Patent Application No. PCT/US2018/043961, 6 pages, dated Nov. 23, 2018.
Kato, Patch used for treating Alzheimer-type dementia, comprises support portion, adhesive layer, donepezil and/or its hydrochloride, and additive chosen from isostearic acid, 2-cetyl ethylhexanoate, and hexadecyl isostearate, Database WPI, AN 2014-C88308 (2014).
Pastore et al., "Transdermal patches: history, development and pharmacology", Br. J. Pharmacol., vol. 172, No. 9, pp. 2179-2209 (2015).
Ravi and Gupta, "The treatment of alzheimers disease by using donepezil loaded transdermal patch", J. Chem. Pharm. Res., vol. 7, No. 3, pp. 806-813 (2015).
Schulz et al., "Therapeutic and toxic blood concentrations of nearly 1,000 drugs and other xenobiotics", Crit. Care, vol. 16, No. R136, 4 pgs. (2012).
Sozio et al., "Transdermal donepezil on the treatment of Alzheimer's disease", Neuropsychiatr. Dis. Treat., vol. 8, pp. 361-368 (2012).
Tiseo et al., "Pharmacokinetic and pharmacodynamic profile of donepezil HCl following evening administration", Br. J. Pharmacol., vol. 46, Suppl. 1, pp. 13-18 (1998).

\* cited by examiner

TRANSDERMAL ADHESIVE COMPOSITION COMPRISING A VOLATILE LIQUID THERAPEUTIC AGENT HAVING LOW MELTING POINT

CROSS-REFERENCE TO RELATED APPLICATIONS

This application claims the benefit of U.S. Provisional Application No. 62/608,460, filed Dec. 20, 2017, which is incorporated by reference herein in its entirety.

TECHNICAL FIELD

The subject matter described herein relates to compositions, devices and methods for the transdermal administration of memantine and other active agents that are a volatile liquid or have a low melting point in an adhesive matrix.

BACKGROUND

Memantine is a N-methyl-D-aspartate (NMDA) receptor antagonist with the chemical structure 3,5-dimethyl-1-adamantanamine:

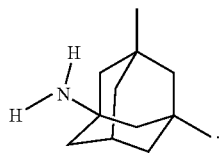

Memantine has a molecular weight of 179.3 and a water solubility of 0.09 mg/mL.

Memantine has been described for use in treating and preventing CNS-related conditions. An oral form of memantine hydrochloride (Namenda®) is approved in the U.S. for use in the treatment of moderate to severe Alzheimer's disease. An oral combination of memantine HCl and donepezil HCl (Namzaric®) is also approved in the U.S. for treatment of Alzheimer's disease. Further, U.S. Pat. No. 3,391,142 to Eli Lilly and Company describes adamantyl secondary amine compounds and their use as antiviral agents. Due to the nature of cognitive disorders, oral medications may be subject to problems with patient compliance especially for formulations that need daily dosing.

Delivery of medications by transdermal, injection, or rectal (suppositories) routes to patients suffering from cognitive disorders has been investigated. U.S. Pat. No. 5,061,703 describes the use of adamantine derivatives in treating cerebral ischemia, which includes Alzheimer's disease treatment. U.S. Pat. No. 8,039,009 describes once daily oral formulations of memantine. U.S. Pat. No. 8,058,291 describes treating a CNS-related condition using an oral dosage form of memantine. U.S. Pat. No. 6,929,801 describes a transdermal delivery device for administering an anti-Parkinson agent such as memantine with a skin-tolerant ester sunscreen. U.S. Pat. No. 8,058,291 describes transdermally administering memantine using a system including an occlusive backing layer that regulates release of the drug from the system. Despite these teachings, there are no memantine transdermal patches or devices available in the United States.

A difficulty with transdermal administration of memantine is the variable skin penetration and loss of active agent from a transdermal device, which is at least partially dependent on the form (free base vs. salt form) of the active. The skin flux varies widely with the form of memantine delivered (free base vs. salt form). Therefore, the skin flux must be carefully controlled in order to prevent or reduce dose dumping, to reduce or control loss of the active agent from the delivery device, and/or to prevent or reduce local skin reactions.

Therefore, there exists a need for transdermal compositions, devices and methods that address these at least these shortcomings.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

It is an object of the present invention to provide methods and compositions to effect transdermal delivery of an active agent such as memantine.

In one aspect, a transdermal delivery system is provided comprising an adhesive matrix. The adhesive matrix is comprised of an adhesive polymer, a solubilizer, and an active agent such as a memantine salt. Preferably, the memantine salt is soluble in the adhesive matrix to at least about 10 mg/mL at 25° C. The memantine salt comprises a counteranion. In embodiments, the counteranion is selected from an alpha-hydroxy carboxylic acid, an aliphatic carboxylic acid, an aromatic carboxylic acid, and a keto acid. In some embodiments, the adhesive matrix comprises at least about 2 w/w % memantine salt. In other embodiments, the adhesive matrix layer comprises about 5-20 w/w % memantine salt. In some embodiments, the alpha-hydroxy carboxylic acid is selected from glycolic acid, lactic acid, and alpha hydroxyl butyric acid. In some embodiments, the keto acid is selected from pyruvic acid, acetoacetic acid, and levulinic acid. In some embodiments, the adhesive matrix comprises between about 5-15 w/w % of the solubilizer. In other embodiments, the solubilizer is present in an amount to achieve a solubility of memantine salt in the adhesive matrix of between about 2-25 w/w % at 25° C. In some embodiments, the solubilizer is a polar solvent. In other embodiments, the solubilizer is selected from propylene glycol, ethylene glycol, glycerol, alkyl alcohol, N-methyl-pyrrolidone, formamide, acetamide, polyethylene glycol, and diethylene glycol monoethyl ether. In some embodiments, the adhesive matrix comprises about 45-90 w/w % of the adhesive polymer. In some embodiments, the adhesive polymer is selected from a polyisobutylene, an acrylic adhesive polymer, a polystyrene block copolymer, a butyl rubber, and a silicone rubber. In some embodiments, the acrylic adhesive polymer is selected from a polyacrylic acid, a methacrylic acid, a polyacrylate, and a polymethacrylate.

It will be appreciated that all w/w % or wt % described herein may refer to wet weight of the formulation including solvent(s) or the dry weight of the formulation.

In some embodiments, the transdermal system further comprises at least one matrix modifier. In embodiments, the matrix modifier is present in the adhesive matrix in an amount between about 2-20 w/w %. In some embodiments, the matrix modifier is selected from a cross-linked polyvinylpyrrolidone, a soluble polyvinylpyrrolidone, fumed silica, colloidal silicone dioxide, a cellulose derivative, a polyacrylamide, a polyacrylic acid, a polyacrylic acid salt, kaolin, bentonite and combinations thereof.

In some embodiments, the transdermal system further comprises a contact adhesive layer in direct or indirect contact with the adhesive matrix, the contact adhesive layer comprising a contact layer adhesive polymer, a contact layer solubilizer, and a contact layer memantine salt soluble in the contact layer solubilizer to at least about 10 mg/mL at 25° C. In some embodiments, the contact layer memantine salt is different from the memantine salt in the adhesive layer. In some embodiments, the contact layer memantine salt comprises a counteranion selected from an alpha-hydroxy carboxylic acid, an aliphatic carboxylic acid, an aromatic carboxylic acid, and a keto acid. In embodiments, the alpha-hydroxy carboxylic acid is selected from glycolic acid, lactic acid, and alpha hydroxyl butyric acid. In embodiments, the keto acid is selected from pyruvic acid, acetoacetic acid, and levulinic acid.

In some embodiments, at least one of the adhesive polymer in the adhesive matrix or the adhesive polymer in the contact layer is selected from a polyisobutylene, an acrylic adhesive polymer, a polystyrene block copolymer, a butyl rubber, and a silicone rubber. In further embodiments, the acrylic adhesive polymer is selected from a polyacrylic acid, a methacrylic acid, a polyacrylate, and a polymethacrylate.

In some embodiments, the solubilizer used in the adhesive layer and/or the contact layer solubilizer is selected from at least one of propylene glycol, ethylene glycol, glycerol, alkyl alcohol, N-methyl-pyrrolidone, formamide, acetamide, polyethylene glycol, and diethylene glycol monoethyl ether. In some embodiments, the contact layer adhesive polymer is different from the adhesive polymer used in the adhesive layer. In embodiments, the solubilizer present in the contact layer is different from the solubilizer used in the adhesive layer.

In some embodiments, the adhesive matrix of the delivery system provides an in vitro memantine skin flux of between about 4-15 $\mu g/cm^2$-hr for a period of at least about 2 days.

In another aspect, a formulation for the manufacture of a transdermal delivery system is provided. In some embodiments, the formulation comprises (i) between about 1-20 w/w % memantine base; (ii) between about 30-60 w/w % of an adhesive polymer; (iii) between about 1-15 w/w % of a solubilizer; (iv) between about 1-10 w/w % of a counteranion; and (v) between about 1-25 w/w % of a matrix modifier where all weights are dry weight.

In some embodiments, the counteranion is selected from one or more of an alpha-hydroxy carboxylic acid, an aliphatic carboxylic acid, an aromatic carboxylic acid, and a keto acid. In further embodiments, the alpha-hydroxy carboxylic acid is selected from glycolic acid, lactic acid, and alpha hydroxyl butyric acid. In additional embodiments, the keto acid is selected from pyruvic acid, acetoacetic acid, and levulinic acid.

In a further aspect, a method of transdermally administering an active agent such as memantine to a subject in need thereof is provided. In some embodiments, the method includes the step of providing a transdermal drug delivery system as described herein or a transdermal drug delivery system that is prepared using the formulations as described herein. In some embodiments, the method also includes administering or instructing the subject or medical personnel to administer the transdermal drug delivery system to the skin of the subject which achieves a therapeutic blood concentration of memantine for between about 3-7 days. In some embodiments, the therapeutic blood concentration of the active agent is an amount effective for treating Alzheimer's disease.

In an additional aspect, a method of treating Alzheimer's disease is provided. In some embodiments, the method includes providing a transdermal drug delivery system as described herein or a transdermal drug delivery system that is prepared using the formulations as described herein to a subject in need thereof.

DETAILED DESCRIPTION

I. Definitions

Figure 1A:
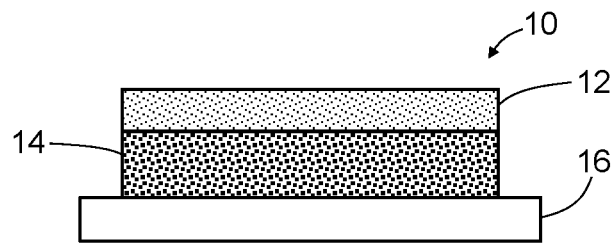
FIGS. 1A-1C are illustrations of embodiments of transdermal delivery system configurations.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

The present compositions, devices, and methods are not limited to the specific polymers, excipients, cross-linking agents, additives, manufacturing processes, or adhesive products described herein. It will be understood that the particular terminology used herein is for the purpose of describing particular embodiments and is not intended to be limiting.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The use of terms of order or importance, including "first" and "second", is to distinguish and identify individual elements and does not denote or imply a particular order or importance unless clearly indicated by context.

The term "active agent" as used herein refers to a chemical material or compound suitable for topical or transdermal administration and that induces a desired effect. The terms include agents that are therapeutically effective, prophylactically effective, and cosmetically effective agents. The terms "active agent", "drug" and "therapeutic agent" are used interchangeably herein.

"Memantine" as used herein refers to 3,5-dimethyl-1-adamantanamine. Memantine may refer to the active agent in base form or as a salt.

The term "therapeutically effective amount" as used herein refers to the amount of an active agent that is nontoxic but sufficient to provide the desired therapeutic effect. The amount that is "effective" will vary from subject to subject, depending on the age and general condition of the individual, the particular active agent or agents, and the like as known to those skilled in the art.

The terms "transdermal" or "transdermal delivery" as used herein refer to administration of an active agent to a body surface of an individual so that the agent passes through the body surface, e.g., skin, and into the individual's blood stream. The term "transdermal" is intended to include transmucosal administration, i.e., administration of a drug to the mucosal (e.g., sublingual, buccal, vaginal, rectal) surface of an individual so that the agent passes through the mucosal tissue and into the individual's blood stream.

II. Compositions/Devices

The compositions and devices described herein are designed for transdermal administration of an active agent such as memantine. The compositions may be used in devices, patches or systems suitable for transdermal delivery of the agent. The compositions described herein are contemplated for use in transdermal delivery systems, devices and/or methods as described further below. The systems and/or devices described herein are contemplated for use in methods as described further below. The active agent is discussed with reference to memantine below. However, it will be appreciated that the discussion is applicable to other suitable active agents.

Figure 1B:
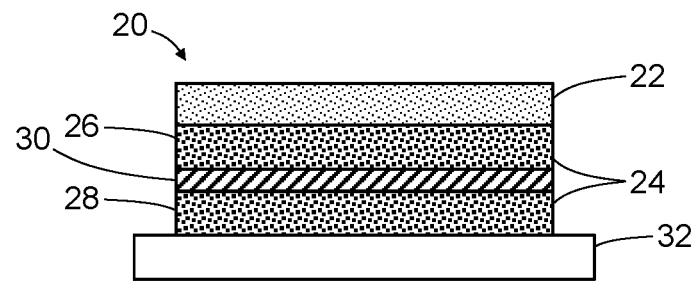
Figure 1C:
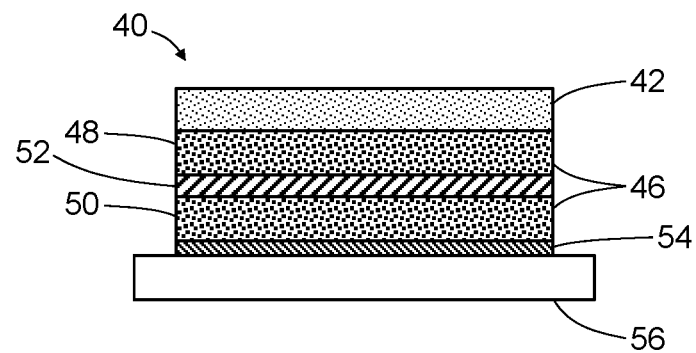

Some exemplary devices are shown in FIGS. 1A-1C. FIG. 1A illustrates a transdermal device 10 including a backing layer 12, an adhesive matrix 14, which comprises the active agent, and an optional release liner 16. FIG. 1B illustrates another embodiment of a transdermal device 20 including multiple adhesive matrix layers 24. The device 20 includes a backing layer 22, a first adhesive layer 26 and a second adhesive layer 28. One or more of the first and second adhesive layers includes at least one active agent. In embodiments where the first and second adhesive layers both comprise an active agent, the first and second adhesive layers may comprise the same or different active agents. The first and second adhesive layers may be separated by a layer such as a nonwoven tie layer 30. The device further includes an optional release liner 32. FIG. 1C illustrates a further embodiment of a transdermal device 40 also including multiple adhesive matrix layers 46. The device 40 includes a backing layer 42, a first adhesive layer 48 and a second adhesive layer 50. One or more of the first and second adhesive layers includes one or more active agents. In embodiments where the first and second adhesive layers both comprise an active agent, the first and second adhesive layers may comprise the same or different active agents. The first and second adhesive layers may be separated by a layer such as a nonwoven tie layer 52. The device may further comprise a contact adhesive layer 54. The contact adhesive layer may be in direct or indirect contact with one of the adhesive layers. In the embodiment as shown in FIG. 1C, the contact adhesive layer is adjacent the second adhesive layer 50. The contact adhesive layer 54 may comprise one or more active agents, which may be the same or different from active agents in the first and/or second adhesive layers. The device further includes an optional release liner 56.

In some embodiments, the backing layer 12, 22, 42 provides a structural element for holding or supporting the adhesive layer. The backing layer may be formed of any suitable material as known in the art. In some embodiments, the backing layer is occlusive. In some embodiments, the backing is preferably impermeable or substantially impermeable to moisture. In one exemplary embodiment, the barrier layer has an MVTR (moisture vapor transmission rate) of less than about 50 g/m$^2$-day. In some embodiments, the backing layer is preferably inert and/or does not absorb components of the adhesive layer, including the active agent. In some embodiments, the backing layer preferably prevents release of components of the adhesive layer through the backing layer. The backing layer may be flexible or non-flexible. The backing layer is preferably at least partially flexible such that the backing layer is able to conform at least partially to the shape of the skin where the patch is applied. In some embodiments, the backing layer is flexible such that the backing layer conforms to the shape of the skin where the patch is applied. In some embodiments, the backing layer is sufficiently flexible to maintain contact at the application site with movement, e.g. skin movement. Typically, the material used for the backing layer should permit the device to follow the contours of the skin or other application site and be worn comfortably on areas of skin such as at joints or other points of flexure, that are normally subjected to mechanical strain with little or no likelihood of the device disengaging from the skin due to differences in the flexibility or resiliency of the skin and the device.

In some embodiments, the backing layer is formed of one or more of a film, non-woven fabric, woven fabric, laminate, and combinations thereof. In some embodiments, the film is a polymer film comprised of one or more polymers. Suitable polymers are known in the art and include elastomers, polyesters, polyethylene, polypropylene, polyurethanes and polyether amides. In some embodiments, the backing layer is formed of one or more of polyethylene terephthalate, various nylons, polypropylene, metalized polyester films, polyvinylidene chloride, and aluminum foil. In some embodiments, the backing layer is a fabric formed of one or more of polyesters such as polyethylene terephthalate, polyurethane, polyvinyl acetate, polyvinylidene chloride and polyethylene. In one particular, but non-limiting embodiment, the backing layer is formed of a polyester film laminate. One particular polyester film laminate is the polyethylene and polyester laminate such as the laminate sold under the name Scotchpak™ #9723.

The device includes at least one adhesive layer 14, 26, 28, 48, 50, 54. In embodiments, at least one of the adhesive layers is an adhesive matrix comprising one or more active agents as described below. The adhesive layer adheres to the backing layer, an adjacent adhesive layer, a tie layer, a release liner and/or skin at the administration site. The adhesive layer matrix also serves to release the active agent to the skin. In embodiments, one or more of the first adhesive layer, the second adhesive layer and/or the contact layer are formed of an adhesive matrix.

In embodiments, the device includes a release liner 16, 32, 56 at least partially in contact with at least one of the adhesive layers to protect the adhesive layer(s) prior to application. The release liner is typically a disposable layer that is removed prior to application of the device to the treatment site. In some embodiments, the release liner preferably does not absorb components of the adhesive layer(s), including the active agent. In some embodiments, the release liner preferably impermeable to components of the adhesive layer(s) (including the active agent) and prevents release of components of the adhesive layer(s) through the release liner. In some embodiments, the release liner is formed of one or more of a film, non-woven fabric, woven fabric, laminate, and combinations thereof. In some embodiments, the release liner is a silicone-coated polymer film or paper. In some non-limiting embodiments, the release liner is a silicone-coated polyethylene terephthalate (PET) film, a fluorocarbon film, or a fluorocarbon coated PET film.

In some embodiments, the device further includes one or more fabric or tie layers 30 and 52 within or between the adhesive layers. In some embodiments, a tie layer is useful to increase bonding between layers of the device. Tie layers may increase bonding by providing chemical groups for the polymers to bind. In other embodiments, the tie layer is useful as a separation for the adhesive matrix layers. The tie layer may be formed of any suitable material including, but not limited to, polyesters, vinyl acetate polymers and copolymers, polyethylenes, and combinations thereof. In one embodiment, the tie layer is a nonwoven layer of polyester fibers such as the film sold under the name Reemay® (Kavon Filter Products Co.). In embodiments, the tie layer does not affect the rate of release of the active agent from the adhesive layers. It will be appreciated that a tie layer may be included between one, some or all of the adhesive matrix layers.

In one embodiment, the transdermal device includes memantine as the active agent in one or more of the first adhesive layer, the second adhesive layer and/or the contact layer. Memantine in free base form is a liquid which is miscible with adhesives such as acrylates, silicone adhesives, and polyisobutylene such as those typically used in forming transdermal delivery devices. Memantine in free base form is typically highly permeable to adhesive matrix systems used in transdermal delivery devices. Memantine free base is also highly permeable to the skin. Thus, memantine in free base form has a high skin flux rate from transdermal adhesive matrices. For safe and long term transdermal dosing, the skin flux of memantine from the adhesive matrix must be controlled in order to prevent dose dumping and local skin reactions. Low loading the memantine base in the adhesive matrix can achieve reduced permeation of the drug; however, the total amount of drug available for delivery from the device (deliverable drug) is limited by the low loading and does not provide sustained delivery over a period of days. In some embodiments, the transdermal device is useful for transdermal dosing of memantine as opposed to topical use. In these embodiments, topical uses of memantine such as use as a sunscreen are precluded.

The salt form of memantine (e.g. memantine HCl) has a negligible or low solubility in adhesive matrices, which depends on the chemical nature of the adhesive polymer. Memantine salt consequently has a low dissolution/diffusion rate from a transdermal matrix. Use of a memantine salt in the adhesive matrix can achieve a solubility of the active in the range of 2% to 25% with or without the use of a solubilizer.

Solvent-cast processes as often used in preparing transdermal delivery devices cause significant loss of the active agent due to attrition in the drying process(es).

In one aspect, compositions and formulations for transdermal delivery of memantine or other suitable active agents are provided. In particular, the formulations and compositions provide a controlled rate of delivery of memantine in an amount sufficient for therapy for conditions responsive to memantine that is suitable for to provide delivery of a suitable dose of memantine over a desired period of time. In embodiments, the formulations used in the preparation of adhesive matrices for a transdermal delivery device comprise memantine in the base form. The adhesive matrices of the transdermal delivery device comprise memantine in a salt form or as an ion-pair/salt form. In embodiments, the formulations and compositions discussed below are useful for preparing one or more adhesive layer and/or the contact layer. Exemplary compositions and formulations were prepared and are described in Examples 1-5.

In some embodiments, the formulations and compositions comprise memantine in a delivery vehicle. In some embodiments, the delivery vehicle is an adhesive matrix. In embodiments, the adhesive matrix comprises at least one adhesive polymer, at least one solubilizer, and a memantine salt or memantine ion-pair/salt. Preferably, the memantine salt is soluble in the delivery vehicle to at least about 10 mg/mL at 25° C. In some embodiments, the memantine salt in the contact layer, where present, is soluble in the contact layer adhesive polymer to at least about 10 mg/mL at 25° C. In other embodiments, the memantine salt is soluble in the adhesive matrix to at least about 1% w/w. In some embodiments, the adhesive matrix comprises at least one counteranion. Partial or complete solubilization of the memantine salt in the adhesive matrix can be used to control the diffusion rate of the drug in the matrix, which is used to control the skin permeation rate. Inclusion of the solubilizer in the adhesive matrix increases the solubility of the drug, which increases drug loading in the adhesive matrix. In some embodiments, the formulations provide delivery of the drug from the delivery vehicle at a controlled rate of not more or higher than about 20 $\mu g/cm^2/hr$. In other embodiments, the formulations provide delivery of the drug from the delivery vehicle at a controlled rate of not more or higher than about 10 or 15 $\mu g/cm^2/hr$. In embodiments, the formulations provide delivery of the drug from the delivery vehicle at a controlled rate of not more or higher than about 5-20 $\mu g/cm^2/hr$.

In some embodiments, the components of the delivery vehicle are tailored to provide delivery of the drug from the delivery vehicle over a period of about 3-10 days or more. In some embodiments, the delivery period is between about 3-4 days, 3-5 days, 3-6 days, 3-7 days, 3-8 days, 4-5 days, 4-6 days, 4-7 days, 4-8 days, 4-9 days, 4-10 days, 5-6 days, 5-7 days, 5-8 days, 5-9 days, 5-10 days, 6-10 days, 7-10 days, 8-10 days, or 9-10 days, inclusive. In some embodiments, the components of the delivery vehicle are tailored to provide transdermal adsorption and/or delivery of the active agent in an amount sufficient for therapy for a period of time selected of at least about 1 day, 2 days, 3 days, 4 days, 5 days, 6 days, 7 days, 8 days, 9 days, 10 days, or more. In some embodiments, the drug is released from the adhesive matrix as a continuous and/or sustained release over the delivery period.

In some embodiments, memantine is added to the formulation in the free base form along with a suitable counteranion. The memantine base and counteranion at least partially interact in the formulation to form a memantine salt in the adhesive matrix. Percentages as described below apply to the memantine base and/or memantine salt present in the formulation and/or the resulting adhesive matrix. In some embodiments, memantine is added, included and/or present in the formulations in an amount of at least about 2 w/w %. In embodiments, selection of the counteranion to achieve selection of the salt, selection of the components of the adhesive matrix, and/or selection of the solubilizers is used to achieve a solubility of the memantine ion pair of at least or not less than about 2 w/w %. In other embodiments, selection of the adhesive matrix components is used to achieve a solubility of the memantine salt in the matrix of at least about 2-25%. In other embodiments, selection of the adhesive matrix components is used to achieve a solubility of the memantine salt in the matrix of at least about 10 mg/mL of the adhesive matrix.

In some embodiments, memantine is added, included and/or present in the formulation and/or matrix in an amount of between about 1-30 w/w % or 2-30 w/w %. In some embodiments, memantine is added, included and/or present in the formulation and/or matrix in an amount of between about 1-20 w/w %, 1-15 w/w %, 1-10 w/w %, 1-5 w/w %, 2-20 w/w %, 2-15 w/w %, 2-10 w/w %, 2-5 w/w %, 5-30 w/w %, 5-20 w/w %, 5-15 w/w %, 5-13 w/w %, 5-12 w/w %, 5-11 w/w %, 5-10 w/w %, 5-9 w/w %, 5-8 w/w %, 8-30 w/w %, 8-20 w/w %, 8-15 w/w %, 8-13 w/w %, 8-12 w/w %, 8-11 w/w %, 8-10 w/w %, 9-30 w/w %, 9-20 w/w %, 9-15 w/w %, 9-13 w/w %, 9-12 w/w %, 9-11 w/w %, 9-10 w/w %, 10-30 w/w %, 10-20 w/w %, 10-15 w/w %, 10-13 w/w %, 10-12 w/w %, 10-11 w/w %, 11-30 w/w %, 11-20 w/w %, 11-15 w/w %, 11-13 w/w %, 11-12 w/w %, 12-30 w/w %, 12-20 w/w %, 12-15 w/w %, 12-13 w/w %, 13-3-w/w %, 13-20 w/w %, or 13-15 w/w % (inclusive of sub-ranges). In some non-limiting embodiments, memantine is added, included and/or present in the formulation and/or matrix in an amount of at least about 1 w/w %, 2 w/w %, 5 w/w %, 8 w/w %, 9 w/w %, 10 w/w %, 11 w/w %, 12 w/w %, 13 w/w %, 14 w/w %, 15 w/w %, 20 w/w %, 30 w/w %. In some embodiments, memantine is included in the formulations and/or matrix as a salt form. It will be appreciated that memantine may be added, included and/or present in the adhesive matrix in base and/or salt form. In some embodiments, memantine is added, included and/or present in different layers of the adhesive matrix in different forms. For example, where the adhesive matrix includes a drug reservoir type layer and a contact adhesive type layer, memantine may be included in the reservoir layer as a memantine salt and in the contact layer as memantine base, or vice versa.

In embodiments, the formulations are formed by addition of memantine base and at least one counteranion. The memantine and counteranion will react during manufacture of the delivery vehicle to form a memantine salt or memantine ion-pair/salt. In some embodiments, memantine is added to the formulation as the memantine base, which is miscible with adhesive polymers. However, memantine base is highly permeable to the skin and has a high dissolution rate from the adhesive matrix. Due to the presence of the counteranion, memantine is present in the adhesive matrix in a salt form in order to regulate dissolution from the adhesive matrix and therefore to control skin flux. As described further below, one or more solubilizers may be used to tailor the dissolution rate of the drug from the adhesive matrix.

In embodiments, a counteranion is added, included and/or present in the formulation and/or matrix in an amount of between about 1-20 w/w % or about 4-20 w/w %. In some embodiments, the counteranion is added, included and/or present in the formulation and/or matrix in an amount of between about 1-15 w/w %, 1-10 w/w %, 1-9 w/w %, 1-8 w/w %, 1-7.5 w/w %, 1-7 w/w %, 1-6 w/w %, 1-5 w/w %, 4-15 w/w %, 4-10 w/w %, 4-9 w/w %, 4-8 w/w %, 4-7.5 w/w %, 4-7 w/w %, 4-6 w/w %, 4-5 w/w %, 5-15 w/w %, 5-10 w/w %, 5-9 w/w %, 5-8 w/w %, 5-7.5 w/w %, 5-7 w/w %, 5-6 w/w %, 6-15 w/w %, 6-10 w/w %, 6-9 w/w %, 6-8 w/w %, 6-7.5 w/w %, 6-7 w/w %, 7-15 w/w %, 7-10 w/w %, 7-9 w/w %, 7-8 w/w %, 7-7.5 w/w %, 7.5-15 w/w %, 7.5-10 w/w %, 7.5-9 w/w %, 7.5-8 w/w %, 7-10 w/w %, 7-9 w/w %, 7-8 w/w %, 7-7.5 w/w %, 8-15 w/w %, 8-10 w/w %, 8-9 w/w %, or 9-10 w/w %. In some specific, but not limiting, embodiments, the counteranion is added, included and/or present in the formulation and/or matrix in an amount of about 1 w/w %, 2 w/w %, 4 w/w %, 4.5 w/w %, 4.75 w/w %, 5 w/w %, 5.25 w/w %, 5.5 w/w %, 5.75 w/w %, 6 w/w %, 6.5 w/w %, 7 w/w %, 7.25 w/w %, 7.5 w/w %, 7.75 w/w %, 8 w/w %, 8.5 w/w %, 9 w/w %, 9.25 w/w %, 9.5 w/w %, 9.75 w/w %, 10 w/w % or about 20 w/w % (inclusive of sub-ranges).

In another embodiment, a counterion selected from one or more of an alpha-hydroxy carboxylic acid, an aliphatic carboxylic acid, and an aromatic carboxylic acid, is included in the formulation in a equimolar or greater than equimolar amount of the moles of memantine in the formulation. In one embodiment, the molar ratio of the compound providing the counterion to memantine is equal to or greater than about 1, 1.05, 1.1, 1.2, 1.25, 1.3, 1.35, 1.4, 1.45, 1.5, 1.55, 1.60, 1.65, 1.7, 1.75, 1.8, 1.9 or 2.0. In one embodiment, the molar ratio of levulinc acid (as a model for the compound providing the counterion) to memantine base is greater than equimolar.

In embodiments, the counteranion is an organic acid. In some embodiments, the counteranion is a carboxylic acid or a keto acid. In embodiments, the carboxylic acid is selected from one or more of an alpha-hydroxy carboxylic acid, an aliphatic carboxylic acid, an aromatic carboxylic acid. In embodiments, the alpha-hydroxy carboxylic acid is selected from one or more of glycolic acid, lactic acid, and alpha-hydroxyl butyric acid. In embodiments, the keto acid is selected from one or more of pyruvic acid, acetoacetic acid, and levulinic acid.

In embodiments, the adhesive matrix comprises memantine salt comprising a counteranion selected from an alpha-hydroxy carboxylic acid, an aliphatic carboxylic acid, an aromatic carboxylic acid, and a keto acid as described above. In some embodiments, the adhesive matrix does not comprise memantine HCl.

In embodiments, the formulations and/or matrix comprise one or more solubilizers. In some embodiments, the adhesive matrix comprises between about 1-25 w/w % of the solubilizer. In some embodiments, the memantine is added, included and/or present in the formulation and/or matrix in an amount of between about 1-20 w/w %, 1-15 w/w %, 1-10 w/w %, 1-5 w/w %, 5-25 w/w %, 5-20 w/w %, 5-15 w/w %, 5-10 w/w %, 10-25 w/w %, 10-20 w/w %, 10-15 w/w %, 15-25 w/w %, 15-20 w/w %, or 20-25 w/w % (inclusive of sub-ranges). In one embodiment, the formulation comprises an amount of memantine to provide a molar amount that is less than the molar amount of the compound with the counterion in the formulation, e.g., levulinic acid or any of the other counterion compounds disclosed herein.

In other embodiments, the solubilizer is present in an amount to achieve a desired solubility of the active agent such as the memantine salt in the adhesive matrix. In some embodiments, an amount of solubilizer is added to the formulation and/or matrix to achieve a solubility of memantine salt of between about 2-25 w/w % at about 20-25° C. In some embodiments, the solubilizer is added, included and/or present in the formulation and/or matrix in an amount to achieve a solubility of the active agent in the formulation and/or matrix of about 2-20 w/w %, 2-15 w/w %, 2-10 w/w %, 2-5 w/w %, 5-25 w/w %, 5-20 w/w %, 5-15 w/w %, 5-10 w/w %, 10-25 w/w %, 10-20 w/w %, 10-15 w/w %, 15-25 w/w %, 15-20 w/w %, or 20-25 w/w % (inclusive of sub-ranges). In some specific, but not limiting embodiments, the solubilizer is added, included and/or present in the formulation and/or matrix in an amount of about 2 w/w %, 5 w/w %, 10 w/w %, 15 w/w %, 20 w/w %, and 25 w/w %.

Where the device includes two or more adhesive layers, it will be appreciated that the different layers may utilize different solubilizers or solubilizer combinations. For example, in the embodiments shown in FIGS. 1B and 1C, the contact adhesive layer may comprises a different solubilizer than one or both of the first and second adhesive layers.

In some embodiments, the solubility of memantine achieved is at a temperature of about 20-25° C. In some embodiments, the solubility of memantine is achieved at a temperature of about 20° C. or about 25° C.

In some embodiments, the solubilizer is a polar solvent. In some embodiments, the solubilizer is selected from one or more of propylene glycol, ethylene glycol, glycerol, an alkyl alcohol, N-methyl-pyrrolidone, formamide, acetamide, polyethylene glycol, and diethyl glycol monoethyl ether.

In embodiments, the adhesive polymer matrix comprises one or more adhesive polymers. In some embodiments, the adhesive polymer is selected from one or more of a polyisobutylene, an acrylic adhesive polymer, a polystyrene block copolymer, a butyl rubber, and a silicone rubber. In embodiments, the acrylic adhesive polymer is selected from a polyacrylic acid, a methacrylic acid, a polyacrylate, and a polymethacrylate. In one embodiment, the adhesive polymer comprises a combination, blend or mixture of polyisobutylene and polybutene.

In some embodiments, the adhesive polymer is a blend or a mixture of a high molecular weight polyisobutylene and a medium molecular weight polyisobutylene. The term, "high molecular weight polyisobutylene" refers to a polyisobutylene having an average molecular weight in the range of about 450,000 to about 2,100,000 Daltons, and preferably from about 500,000 to about 1,500,000 Daltons. The term, "medium molecular weight polyisobutylene" refers to a polyisobutylene having an average molecular weight in the range of about 10,000 to about 450,000 Daltons, and preferably from about 25,000 to about 100,000 Daltons.

In some embodiments, the adhesive polymer comprises an acrylic polymer pressure sensitive adhesive. An acrylic polymer pressure sensitive adhesive intends a polyacrylate adhesive that is a polymer or a copolymer of a monomer or monomers selected from acrylic acid esters and methacrylic acid esters. Other monomers, such as acrylic acid and vinyl acetate, may be present. In one embodiment, the acrylate adhesive is not a methacrylate copolymer; that is, the polyacrylate adhesive excludes a methacrylic acid monomeric unit. Preferably the acrylic polymer pressure sensitive adhesive has pendent carboxyl (—COOH) or hydroxyl (—OH) functional groups attached to the polymer chain.

In some embodiments, the acrylic acid/vinyl acetate copolymer is one without a cross-linker agent. The exclusion of cross-linker agents containing metals, particularly transition metal cross-linking agents, which act as catalysts of several chemical reactions, such as esterification, transesterification, oxidation and addition, avoids the possibility of chemical interaction with the active agent in the matrix and a possible loss of potency, impurity formation and stability problems. In embodiments, the matrix does not contain a component acting as a cross-linking agent for the acrylic polymer.

In some embodiments, the formulation and/or matrix comprises about 45-90 w/w % of the one or more adhesive polymer(s). In some embodiments, the formulation and/or matrix comprises about 45-80 w/w %, 45-75 w/w %, 45-70 w/w %, 45-60 w/w %, 45-50 w/w %, 50-90 w/w %, 50-80 w/w %, 50-75 w/w %, 50-70 w/w %, 50-60 w/w %, 60-90 w/w %, 60-80 w/w %, 60-75 w/w %, 60-70 w/w %, 70-90 w/w %, 70-80 w/w %, 70-75 w/w %, 75-90 w/w %, 75-80 w/w %, or 80-90 w/w % of the one or more adhesive polymers (inclusive of sub-ranges).

It will be appreciated that the adhesive polymers may be different between one or more of the adhesive layers of the device. The adhesive layers may use different polymers or different polymer compositions. As one example, the contact layer adhesive polymer is different than the adhesive polymer used in one or both of the first and second adhesive layers as shown in FIG. 1C.

In some embodiments, the formulation and/or matrix comprise at least one or one or more matrix modifiers. Without wishing to be bound by theory, it is believed that the matrix modifier facilitates homogenization of the adhesive matrix. Sorption of hydrophilic moieties is a possible mechanism for this process. Thus, known matrix modifiers which are to some degree water-sorbent may be used. For example, possible matrix modifiers include one or more of a cross-linked polyvinylpyrrolidone (PVP), a soluble polyvinylpyrrolidone (PVP), fumed silica, colloidal silicone dioxide, a cellulose derivative (e.g. hydroxypropyl cellulose (HPC), hydroxyethylcellulose (HEC)), a polyacrylamide, a polyacrylic acid, a polyacrylic acid salt, a clay such as kaolin or bentonite, bentonite and combinations thereof. An exemplary commercial fumed silica product is Aerosil® 200P, an amorphous, anhydrous colloidal silicon dioxide (Evonik Industries). Another exemplary fumed silica product is Cab-O-Sil (Cabot Corporation, Boston, Mass.).

In some embodiments, the matrix modifier is present in the formulation and/or matrix in an amount between about 2-20 w/w %. In some embodiments, the formulation and/or matrix comprises about 2-15 w/w %, 2-10 w/w %, 2-7.5 w/w %, 2-5 w/w %, 2-4 w/w %, 4-20 w/w %, 4-15 w/w %, 4-10 w/w %, 4-7.5 w/w %, 4-5 w/w %, 5-20 w/w %, 5-15 w/w %, 5-10 w/w %, 5-7.5 w/w %, 7.5-20 w/w %, 7.5-15 w/w %, 7.5-10 w/w %, 10-20 w/w %, 10-15 w/w %, or 15-20 w/w % of the one or more matrix modifier (inclusive of sub-ranges).

It will be appreciated that the above formulations and compositions may be used in preparing at least one of the first adhesive layer, the second adhesive layer and/or the contact adhesive layer as shown in FIGS. 1A-1C. It will be appreciated that the formulations used in preparing the first adhesive layer, the second adhesive layer and/or the contact adhesive layer may be the same or different.

It will be appreciated that the resulting adhesive matrix comprises memantine primarily in salt form. In some embodiments, the memantine salt of the at least one of the first adhesive layer or second adhesive layer is different than the memantine salt of the contact layer. As one example, the contact layer 54 of FIG. 1C may comprise a different memantine salt than one or both of adhesive layers 48 and 50.

Adhesive formulations and adhesive matrices were prepared to illustrate the embodiments described herein. Examples 1 and 3-5 set forth exemplary formulations and the resulting adhesive matrices.

The adhesive formulations and matrices may be formed by any suitable methods as known in the art. In some embodiments, the adhesive formulation is prepared by dissolving an amount of the active agent, typically in base form, in a suitable solvent as known in the art. One or more of the other components of the matrix may also be dissolved in this solvent including, but not limited to, the counteranion, the solubilizer and/or the matrix modifier. The polymer is typically dissolved in a suitable solvent as known in the art. As non-limiting examples, toluene dichloromethane may be used for solvation of PIB polymers. The active agent acid ion-pair/salt should be soluble in the solvent used for solvation of the polymer. In some embodiments, the solvent used for solvation of the polymer is not an aliphatic hydrocarbon solvent such as hexane and heptane. The active agent solution and the polymer solution are mixed until homogeneous to form the adhesive formulation.

In some embodiments, the formulations, adhesive matrices and transdermal devices provide a minimum of loss of the active agent during preparation and processing. In some embodiments, the processes and methods for forming the formulations, adhesive matrices and/or devices result in a total loss of active agent during the manufacturing process of less than 5-25% before administration. In some embodiments, the methods result in less than 5-15%, 5-10%, or 10-15% loss of active agent during manufacture of the finished product.

In Example 1, an adhesive formulation was prepared with memantine base and levulinic acid as a counteranion. The adhesive formulation comprised memantine in free base form at about 10 wt %, levulinic acid as a counteranion at 6.5 wt %, an acrylate/vinyl acetate copolymer as an adhesive polymer at about 64.5 wt %, propylene glycol as a solubilizer at about 12 wt %; and fumed silica as a matrix modifier at about 7 wt %. The ability to use an active agent such as memantine in its free base form to prepare the formulation allows for a higher drug load in the adhesive matrix as memantine in free base form is miscible with solvents typically used in forming an adhesive matrix. The use of the counteranion results in a memantine ion-pair/salt in the adhesive matrix. In this embodiment, the molar ratio of levulinic acid to memantine is greater than equimolar, at 1.38. The formulation of Example 1 comprises levulinic acid which acts as the counteranion for memantine base resulting in a memantine/levulinic acid ion-pair/salt in the matrix. Memantine salt has a lower solubility in the adhesive matrix than the memantine base. In some embodiments, memantine salt has a negligible or low solubility in adhesive matrices which may be adjusted using the chemical nature of the adhesive matrix. The low solubility of memantine salt in the matrix results in a low dissolution/diffusion rate from the adhesive matrix. A solubilizer may be used to adjust or tailor the dissolution/diffusion rate of the memantine from the adhesive matrix. Selection of the solubilizer and/or ion pair salt can be used to adjust the solubility of the memantine salt in the formulation. The formulation solubility is related to diffusion rate and/or the net delivery rate. The formulation of Example 1 comprises propylene glycol as a solubilizer. The adhesive formulation of Example 1 was used to prepare a transdermal delivery device having an adhesive matrix as illustrated in FIG. 1A.

In Example 2, a transdermal delivery device having a first and a second adhesive matrix was prepared by coating a first layer of an adhesive formulation on a release liner material, investing a tie layer material over the first adhesive formulation and coating a second adhesive formulation over the tie layer material. A backing layer is placed over the first or second adhesive formulation. It will be appreciated that the composition of the first and second adhesive formulations may be the same or different. It will further be appreciated that the either or both of the first or second adhesive formulations may comprise one or more active agents, which may be the same or different. In one, non-limiting embodiment, the adhesive matrix layer that contacts the skin does not include a counteranion so that the active agent is present in the matrix in the base form. Where the active agent is memantine, the active can be quickly delivered for an initial dose of the active. The skin flux of the active agent in the second (or further) adhesive layers may be delivered at a controlled rate for controlled and/or extended delivery of the active agent. A transdermal delivery device having a first and a second adhesive matrix is illustrated in FIG. 1B.

In Example 3, a first adhesive formulation comprising the active agent in base form at about 13 wt %, an adhesive polymer at about 60 wt %, a counteranion at about 8.5 wt %, a solubilizer at about 12 wt %, and a matrix modifier at about 7 wt % was formed. A second adhesive formulation comprising the active agent in base form at about 9 wt %, an adhesive polymer at about 71 wt %, a counteranion at about 6 wt %, a solubilizer at about 8.6 wt %, and a matrix modifier at about 5 wt % was formed. In each of these formulations, the adhesive polymers were comprised of a polyisobutylene/polybutene mixture. These formulations were used to prepare a transdermal device having a reservoir adhesive matrix (including a tie layer) layer and a contact adhesive matrix layer as illustrated in FIG. 1C. It will be appreciated that the composition of the reservoir and contact adhesive formulations may be the same or different. It will further be appreciated that where the reservoir adhesive layer includes a first and a second layer separated by a tie layer, the first and second reservoir layer formulations may be the same or different. It will further be appreciated that the either, both, or all of the reservoir or contact adhesive formulations may comprise one or more active agents, which may be the same or different. The contact adhesive layer may or may not include a counteranion to adjust the initial release rate of the active agent from the contact layer.

In Example 4, adhesive formulations comprising the active agent in base form at between about 8-11 w/w %, an adhesive polymer at between about 56-71 w/w %, a counteranion at between about 5-8.5 w/w %, a solubilizer at between about 10-12 w/w %, and a matrix modifier at between about 5-15 w/w % were formed. The adhesive polymers were comprised of a polyisobutylene/polybutene mixture or an acrylic acid/vinyl acetate copolymer. In each of the formulations, the counteranion was levulinic acid and the solubilizer was propylene glycol. In these embodiments, the molar ratio of levulinic acid to memantine is greater than equimolar, at 1.38. The matrix modifier was fumed silica or cross-linked polyvinylpyrrolidone.

In Example 5, adhesive formulations for preparing a reservoir adhesive matrix and a contact adhesive matrix were prepared. Adhesive formulations comprising the active agent in base form at between about 10-15 w/w % or in salt form at 15 w/w %, an adhesive polymer at between about 48-66 w/w %, a counteranion at between about 1-9.71 w/w %, a solubilizer at between about 0-12 w/w %, and a matrix modifier at between about 7-20 w/w % were formed were formed for use in a reservoir adhesive matrix layer. The adhesive polymers were comprised of a polyisobutylene/polybutene mixture or an acrylic acid/vinyl acetate copolymer. In each of the reservoir adhesive formulations, the counteranion was levulinic acid and the solubilizer was propylene glycol, where present. The matrix modifier was fumed silica or cross-linked polyvinylpyrrolidone. Where the active agent was included as a salt form (memantine HCl), no counteranion was needed to form a memantine ion-pair/salt. Further, adhesive formulations comprising the active agent in base form at 0-11.14 w/w %, an adhesive polymer at 65.36-82.00 w/w %, a counteranion at 0-7.22 w/w %, a solubilizer at 0-10.29 w/w %, and a matrix modifier at 4.00-20.00 w/w % were formed for use in a contact adhesive matrix layer. The adhesive polymers were comprised of a polyisobutylene/polybutene mixture. In each of the contact adhesive formulations, the counteranion was levulinic acid, where present, and the solubilizer was propylene glycol, where present. The matrix modifier was fumed silica or cross-linked polyvinylpyrrolidone.

One exemplary formulation for the manufacture of a transdermal delivery system comprises between about 1-10 w/w % memantine base, between about 30-60 w/w % of an adhesive polymer, between about 1-10 w/w % of a solubilizer, between about 1-5 w/w % of a counteranion, and between about 1-25 w/w % of a matrix modifier.

It will be appreciated that the formulations described herein for use as the reservoir adhesive layer and the contact adhesive layer may be interchangeable. For example, the formulations described for use in the reservoir adhesive layer may be used in preparing a contact adhesive layer and vice versa.

Figure 2:
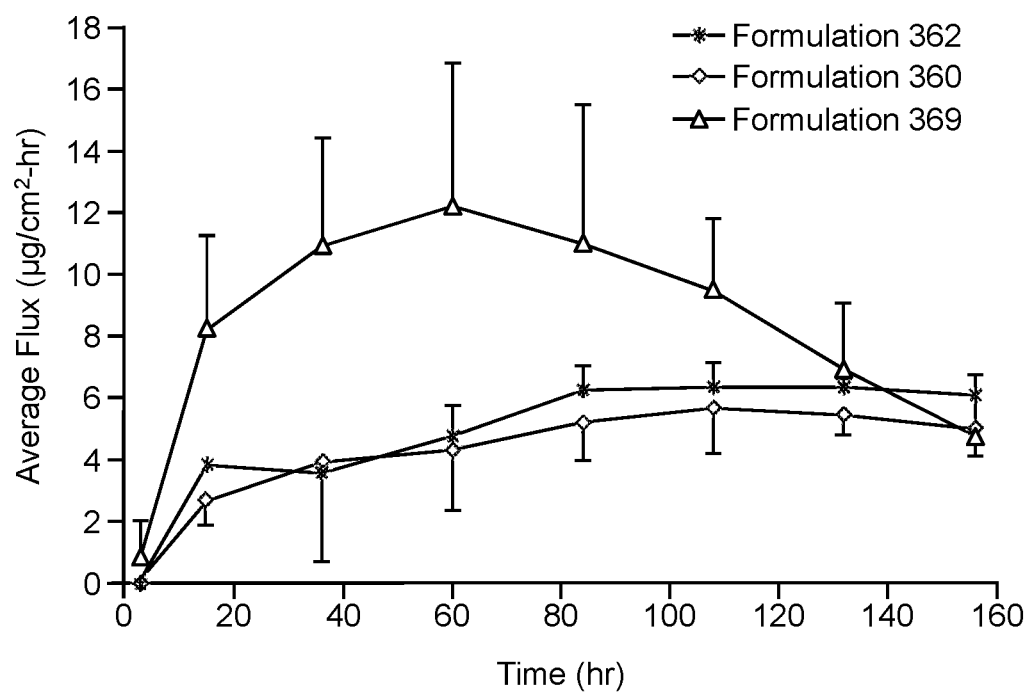
FIG. 2 is a graph of average skin flux for memantine transdermal delivery devices, in $\mu g/cm^2$·hr, in vitro as a function of time, in hours, in an in vitro skin permeation test for devices having the three formulations identified herein as formulations 360 (◊), 362 (*), and 369 (Δ).

In Example 6, formulations prepared with the components described above were tested for in vitro skin flux. FIG. 2 is a graph showing the flux of the formulations identified as nos. 360, 362, and 369. Formulation 360 comprised about 8 w/w % memantine in base form as the active agent, about 62 w/w % of an acrylic acid/vinyl acetate copolymer as the adhesive polymer, about 5.2 w/w % levulinic acid as the counteranion, about 10 w/w % propylene glycol as a stabilizer, and about 15 w/w % of cross-linked polyvinylpyrrolidone as a matrix modifier. Formulation 362 comprised about 10 w/w % memantine in base form as the active agent, about 64 w/w % of an acrylic acid/vinyl acetate copolymer as the adhesive polymer, about 6.5 w/w % levulinic acid as the counteranion, about 12 w/w % propylene glycol as a stabilizer, and about 7 w/w % of fumed silica as a matrix modifier. The average flux for formulation 362 over a 7 day period was about 6.30 µg/cm$^2$/hour. Formulation 369 included both a reservoir adhesive functional layer and a contact adhesive functional layer. The reservoir adhesive layer comprised about 13 w/w % memantine in base form as the active agent, about 60 w/w % of a polyisobutylene/polybutene mixture as the adhesive polymer, about 8 w/w % levulinic acid as the counteranion, about 12 w/w % propylene glycol as a stabilizer, and about 7 w/w % of fumed silica as a matrix modifier. The contact adhesive layer comprised about 9 w/w % memantine in base form as the active agent, about 71 w/w % of a polyisobutylene/polybutene mixture as the adhesive polymer, about 6 w/w % levulinic acid as the counteranion, about 9 w/w % propylene glycol as a stabilizer, and about 5 w/w % of fumed silica as a matrix modifier.

As seen in FIG. 2, formulation 360 (diamonds) had the lowest skin flux over the measurement period. Formulation 360 comprised the lowest initial w/w % of the active agent. Formulation 362 (* symbols) had a higher average skin flux than formulation 360 (6.30 as compared to 4.83 µg/cm$^2$/hour) although both formulations had a steady release rate over the measured time period. Formulation 369 (triangles), which included both a reservoir adhesive layer and a contact adhesive layer, had a significantly higher skin flux over most of the measurement period. Without being limited as to theory, the increase skin flux may be due, at least in part, to the content of the ion pair and/or the matrix modifier content. As seen in FIG. 2, the skin flux rose to about 12 µg/cm$^2$/hour over the first 60 hours and then decreased to about the same skin flux as formulations 360 and 362. As seen in the figure, each of the formulations prepared had a skin flux of less than 20 µg/cm$^2$/hour.

In embodiments, the transdermal devices or systems described herein provide an in vitro memantine skin flux of between about 4-15 µg/cm$^2$/hour for a period of at least about 1-10 days. In some embodiments, the transdermal devices or systems provide an in vitro memantine skin flux of between about 4-12 µg/cm$^2$/hour, 4-10 µg/cm$^2$/hour, 4-7.5 µg/cm$^2$/hour, 5-15 µg/cm$^2$/hour, 5-12 µg/cm$^2$/hour, 5-10 µg/cm$^2$/hour, 5-7.5 µg/cm$^2$/hour, 7.5-15 µg/cm$^2$/hour, 7.5-12 µg/cm$^2$/hour, 7.5-10 µg/cm$^2$/hour, 10-15 µg/cm$^2$/hour, 10-12 µg/cm$^2$/hour, or 12-15 µg/cm$^2$/hour for a period of at least about 1-5 days. In embodiments, the transdermal devices for systems provide the above skin flux for a period of about 1-5 days, about 2-5 days, about 2-10 days, or about 5-10 days. In embodiments, the transdermal devices for systems provide the above skin flux for a period of about 1, 2, 3, 4, 5, 6, 7, 8, 9, or 10 days.

The transdermal devices and systems may be prepared by any suitable methods as known in the art. In some general embodiments, the transdermal devices are prepared by coating an appropriate amount of an adhesive polymer formulation (with or without an active agent) as described above onto a substrate such as a release liner or a backing layer. In one embodiment, the formulation is coated onto the release liner. In some embodiments, the formulation is coated onto the substrate or liner to a desired thickness. The thickness and/or size of the device and/or adhesive matrix may be determined by one skilled in the art based at least on considerations of wearability and/or required dose. It will be appreciated that the administration site for the device will affect the wearability considerations due to the available size of the administration site and the use of the administration site (e.g. need for flexibility to support movement). In some embodiments, the device and/or adhesive matrix has a thickness of between about 25-500 µm. The formulation and substrate are at least partially dried to remove any solvents. A release liner or backing layer is applied to the opposite side of the substrate. Where the substrate is not a release liner or backing layer, the substrate is replaced with the appropriate of a release liner or a substrate. In embodiments that include multiple adhesive polymer layers, a first formulation is applied or coated onto the substrate, a tie layer material is applied to the formulation, and the second adhesive formulation is applied to the tie layer material. The formulation and tie layers are laminated using any suitable methods known in the art. In some embodiments, the adhesive layers are coated onto separate substrates or liners and then joined to form the transdermal delivery device. Where the delivery device includes a reservoir adhesive layer and a contact adhesive layer, the appropriate formulations may be coated onto the substrate or liner and laminated. It will be appreciated that any or all of the formulation layers maybe dried before laminating the layers. In this regard, manufacture of an adhesive matrix comprising memantine with a counterion as described herein offers a benefit in the manufacture. Memantine free base is a volatile liquid that vaporizes during manufacture of an adhesive matrix that is prepared from a solution casting process and dried above room temperature, it is difficult to control memantine content in the final product. That is, an adhesive matrix with memantine is typically prepared from a liquid formulation comprising memantine, adhesive polymers, and other ingredients solubilized in a processing solvent. The liquid formulation is cast onto a substrate and dried, typically above room temperature, to form an adhesive matrix. Memantine in the form of free base in the liquid formulation evaporates during the drying step of the manufacturing process, leading to non-uniform drug content in the finished adhesive matrix. A memantine salt comprising a memantine and a counteranion selected from an alpha-hydroxy carboxylic acid, an aliphatic carboxylic acid, an aromatic carboxylic acid, and a keto acid, as described herein, solves this problem as the salt forms of memantine described herein are not vaporized during the drying step of the manufacturing process.

III. Methods of Treatment

Based on the exemplary compositions and devices described herein, and the data showing release of memantine from the adhesive, skin-contacting layer, methods for treating a suitable condition with memantine are provided herein. In embodiments, compositions and devices comprising memantine are useful for treating, delaying progression, delaying onset, slowing progression, preventing, providing remission, and improvement in symptoms of cognitive disorders or disease are provided herein. In embodiments, compositions and devices comprising memantine are provided for maintaining mental function including, but not limited to a least one of maintaining thinking, memory, speaking skills as well as managing or moderating one or more behavioral symptoms of a cognitive disorder or disease. In embodiments, the cognitive disorder is Alzheimer's disease. In particular embodiments, the cognitive disorder is Alzheimer's type dementia. In embodiments, compositions and devices comprising memantine are provided for use in treating, etc. mild, moderate, or severe Alzheimer's disease.

Alzheimer's disease is the most common cause of senile dementia and is characterized by cognitive deficits related to degeneration of cholinergic neurons. Alzheimer's affects 6-8% of people over the age of 65 and nearly 30% of people over the age of 85 (Sozio et al., *Neurophsychiatric Disease and Treatment*, 2012, 8:361-368), involving the loss of cognitive functioning and behavioral abilities. The causes of Alzheimer's disease are not yet fully understood. As Alzheimer's disease is associated with reduced levels of several cerebral neurotransmitters including acetylcholine (Ach), current treatment includes administering cholinesterase inhibitors. Cholinesterase inhibitors reduce the hydrolysis of acetylcholine in the synaptic cleft by inhibiting cholinesterase and/or butyrylcholinesterase, which increases acetylcholine levels resulting in improved neurotransmission (Sozio et al.).

The transdermal devices described herein may be designed for long term use and/or continuous administration of the active agent. The FDA has approved daily oral doses of memantine of 5 mg, 10 mg, 15 mg, 20 mg, and 28 mg. It will be appreciated that the total dose of the active agent per transdermal device will be determined by the size of the device and the loading of the active agent within the adhesive matrix. In some embodiments, the active agent is released from the adhesive matrix as a continuous and/or sustained release over the application period.

IV. Examples

The following examples are illustrative in nature and are in no way intended to be limiting.

Example 1

Preparation of Transdermal Device Comprising Memantine

An adhesive formulation was prepared by dissolving 10 g memantine base in a mixture of 82.42 g ethyl acetate, 4.34 g. isopropyl alcohol, 12 g of propylene glycol, and 6.48 g levulinic acid to form a clear solution. An amount of 7.0 g Aerosil 200P was added and the solution well homogenized using a Silverson homogenizing mixer. An amount of 127.77 g of an acrylic acid/vinyl acetate copolymer (DuroTak 387-2287) solution (solid content, 50.5%) was added to the solution and mixed to form a homogenous mixture. The resulting adhesive matrix had the following composition:

| Adhesive Formulation No. 362 | | |
|---|---|---|
| Active Agent | memantine base | 10 wt % (dry) |
| Adhesive Polymer(s) | acrylate/vinyl acetate copolymer (Duro-Tak 387-2287) | 64.5 wt % (dry) |
| Solubilizer | propylene glycol | 12 wt % (dry) |
| Counteranion | levulinic acid | 6.5 wt % (dry) |
| Matrix Modifier | fumed silica (Aerosil 200P) | 7.0 wt % (dry) |

The adhesive formulation mixture was coated on a silicone coated polyethylene terephthalate (PET) liner and dried in a Werner Mathis coater at 60° C. for 8 minutes to achieve a dry coat weight of 90 g/m$^2$ (GSM). A backing film was placed on the adhesive formulation on the side opposite the PET liner. The resulting device was die-cut to the appropriate size. An illustration of an exemplary device prepared by this method is shown in FIG. 1A.

Example 2

Preparation of Transdermal Device Comprising Multiple Adhesive Layers

An adhesive formulation was prepared as described in Example 1. Two adhesive formulation layers were made by separately coating a first portion and a second portion of the adhesive formulation mixture on separate silicone coated polyethylene terephthalate (PET) liners. The formulation/liners were dried in a Werner Mathis coater at 60° C. for 8 minutes to achieve a dry coat weight of 90 g/m$^2$ (GSM).

The PET liner was removed from a first of the adhesive formulations. A non-woven polyester fabric (e.g. Remay® 2250) was positioned on the second adhesive formulation (on the side opposite the PET liner) and the first adhesive formulation placed on the fabric. The adhesive formulations (and optional fabric) were laminated.

A backing film was placed on the first adhesive formulation on the side opposite the fabric. The resulting device is die-cut to the appropriate size. An illustration of an exemplary device prepared by this method is shown in FIG. 1B.

Example 3

Preparation of Transdermal Device Comprising Multiple Adhesive Layers

A first adhesive formulation was prepared by dissolving 13 g memantine base in a mixture of 110.28 g toluene/isopropyl alcohol (IPA) (1% IPA based on total solvent weight of wet formulation), 12.00 g propylene glycol, and 8.42 g levulinic acid to form a clear solution. An amount of 7.0 g Aerosil 200P was added and the solution well homogenized using a Silverson homogenizing mixer. A polyisobutylene adhesive solution was prepared by mixing 10% high molecular weight polyisobutylene (Oppanol® B-100, 1,000,000 Dalton molecular weight), 50% medium molecular weight polyisobutylene (Oppanol® B-12, 50,000 Dalton molecular weight), and 40% polybutene (Indopol® H-1900) at 60 w/w % adhesive content in toluene. An amount of 99.30 g of the polyisobutylene adhesive solution (solid content 60%) was added to the memantine solution and mixed mechanically to form a homogenous mixture. This adhesive formulation was used to form the reservoir layer below. The resulting adhesive formulation had the following composition:

| Reservoir Adhesive Formulation No. 369 | | |
|---|---|---|
| Active Agent | memantine base | 13 wt % (dry) |
| Adhesive Polymer(s) | Polyisobutylene mixture | 59.6 wt % (dry) |
| Solubilizer | propylene glycol | 12 wt % (dry) |
| Counteranion | levulinic acid | 8.4 wt % (dry) |
| Matrix Modifier | fumed silica (Aerosil 200P) | 7 wt % (dry) |

A second adhesive formulation for the contact adhesive layer was prepared by dissolving 9.286 g memantine base in a mixture of 102.58 g toluene/isopropyl alcohol (1% IPA based on total solvent weight of wet formulation), 8.571 g propylene glycol, and 6.013 g levulinic acid to form a clear solution. An amount of 5.0 g Aerosil 200P was added and the solution well homogenized using a Silverson homogenizing mixer. An amount of 71.13 g of the polyisobutylene adhesive solution described above (solid content 60%) was added to the memantine solution and mixed mechanically to form a homogenous mixture. This adhesive formulation was used to form the contact layer below. The resulting adhesive matrix had the following composition:

| Contact Adhesive Formulation No. 369 | | |
|---|---|---|
| Active Agent | memantine base | 9.3 wt % (dry) |
| Adhesive Polymer(s) | Polyisobutylene mixture | 71.1 wt % (dry) |
| Solubilizer | propylene glycol | 8.6 wt % (dry) |
| Counteranion | levulinic acid | 6 wt % (dry) |
| Matrix Modifier | fumed silica (Aerosil 200P) | 5 wt % (dry) |

The reservoir adhesive formulation was coated onto a silicone-coated polyethylene terephthalate (PET) liner and dried in a Werner Mathis coater at 70° C. for 15 minutes to achieve a coat weight of 90 g/m² (GSM).

The contact adhesive formulation was coated onto a silicone-coated polyethylene terephthalate (PET) liner at a wet thickness of 160 nm. The formulation was dried in a Werner Mathis coater at 70° C. for 10 minutes to achieve a coat weight of 40 g/m² (GSM).

The PET liner was removed from the reservoir adhesive formulation and the reservoir adhesive formulation placed on top of the contact adhesive formulation (opposite the PET liner). A non-woven polyester fabric (e.g. Remay® 2250) may be positioned between the two adhesive layers. The adhesive formulations (and optional fabric) are laminated.

A backing film is placed on the reservoir adhesive formulation on the side opposite the fabric/contact adhesive formulation. The resulting device is die-cut to the appropriate size. A device having a reservoir adhesive layer, fabric layer, and a contact adhesive layer is illustrated in FIG. 1C.

Example 4

Preparation of Transdermal Memantine Formulations

Adhesive formulations were prepared as described in Example 1 to yield an adhesive formulation with the following compositions for use in preparing an adhesive matrix layer:

| | | Composition (w/w %) (dry) | | | | | | |
|---|---|---|---|---|---|---|---|---|
| | Formulation | 342 | 360 | 361 | 362 | 364 | 365 | 366 |
| Active | memantine base | 10 | 8 | 11 | 10 | 13 | 11.1 | 9.3 |
| Polymer | PIB | | | | | 59.6 | 65.4 | 71.1 |
| | Duro-Tak ® 387-2287 | 56.5 | 61.8 | 53.9 | 64.5 | | | |
| Solubilizer | Propylene glycol | 12 | 10 | 13 | 12 | 12 | 10.3 | 8.6 |
| Counteranion | Levulinic acid | 6.5 | 5.2 | 7.1 | 6.5 | 8.4 | 7.2 | |
| Matrix Modifier | Aerosil ® 200P | | | | 7 | 7 | 6 | 5 |
| | Crospovidone ® | 15 | 15 | 15 | | | | |

Example 5

Preparation of Transdermal Memantine Formulations

Adhesive formulations were prepared as described in Example 3 to yield an adhesive formulation with the following compositions for use in preparing a reservoir adhesive matrix layer:

| | | Composition (w/w %) (dry) | | | | | | |
|---|---|---|---|---|---|---|---|---|
| | Formulation | 280 | 279 | 289 | 328 | 368 | 369 | 370 |
| Active | Memantine base | | 15 | 10 | 12 | 13 | 13 | 13 |
| | Memantine HCl | 15 | | | | | | |
| Polymer | PIB | 65 | 57.3 | 65.6 | | 59.6 | 59.6 | 59.6 |
| | Duro-Tak ® 387-2287 | | | | 48.2 | | | |
| Solubilizer | Propylene glycol | | | | 12 | 12 | 12 | 12 |
| Counteranion | Levulinic acid | | 9.7 | 6.5 | 7.8 | 8.4 | 8.4 | 8.4 |
| Matrix Modifier | Aerosil ® 200P | | | | | 7 | 7 | 7 |
| | Crospovidone | 20.0 | 18.0 | 18.0 | 20.0 | | | |

Adhesive formulations were prepared as described in Example 3 to yield an adhesive formulation with the following compositions for use in preparing a contact adhesive matrix layer:

|  | Formulation | \multicolumn{7}{c}{Composition (w/w %) (dry)} |
|---|---|---|---|---|---|---|---|---|
|  |  | 280 | 279 | 289 | 328 | 368 | 369 | 370 |
| Active | Memantine base | 5 |  |  |  | 11.1 | 9.3 | 7.4 |
| Polymer | PIB | 75 | 82 | 82 | 80 | 65.4 | 71.1 | 76.9 |
| Solubilizer | Propylene glycol |  |  |  | 10 | 10.3 | 8.6 | 6.9 |
| Counteranion | Levulinic acid |  |  |  |  | 7.2 | 6 | 4.8 |
| Matrix Modifier | Aerosil 200P |  |  |  |  | 6 | 5 | 4 |
|  | Crospovidone | 20 | 18 | 18 | 10 |  |  |  |

Example 6

In Vitro Skin Permeation

Dried formulations prepared as described in Example 4 were used to prepare transdermal devices as described in Example 2. The devices comprising each of the formulations were tested in vitro for skin flux using a Franz diffusion cell at 32° C. The receiver solution was replaced at every time interval and analyzed using liquid chromatography-mass spectrometry (LCMS). The average flux in $\mu g/cm^2/hour$ over seven days is shown in the table below.

|  | \multicolumn{7}{c}{Formulation} |
|---|---|---|---|---|---|---|---|
|  | 342 | 360 | 361 | 362 | 364 | 365 | 366 |
| Skin Flux ($\mu g/cm^2/hr$) | 6.5 | 4.8 | 5.5 | 6.3 | 8.4 | 7.7 | 6.3 |

Formulations prepared as described in Example 5 were used to prepare transdermal devices as described in Example 3. The devices comprising each of the formulations were tested in vitro for skin flux. The average flux over seven days is shown in the table below.

|  | \multicolumn{7}{c}{Formulation} |
|---|---|---|---|---|---|---|---|
|  | 280 | 279 | 289 | 328 | 368 | 369 | 370 |
| Average Skin Flux ($\mu g/cm^2/hr$) | 0.77 | 10.6 | 8.6 | 6.9 | 8.3 | 10.3 | 8.1 |

The skin flux in $\mu g/cm^2/hour$ for formulations 360, 362 and 369 over 160 hours is shown in FIG. 2.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, and other publications mentioned herein are hereby incorporated by reference in their entirety. Where a patent, application, or publication contains express definitions, those definitions should be understood to apply to the incorporated patent, application or publication in which they are found and not to the present application unless otherwise indicated.

It is claimed:

1. A transdermal delivery system, comprising: an adhesive matrix comprised of an adhesive polymer, a solubilizer, and a memantine salt, the memantine salt consisting of memantine and a levulinic acid counteranion, wherein the adhesive matrix comprises a memantine/levulinic acid ion-pair/salt, and wherein the levulinic acid counteranion is present in an equimolar or greater than equimolar amount relative to memantine.

2. The transdermal system of claim 1, wherein the adhesive matrix comprises between about 5-15 w/w % of the solubilizer.

3. The transdermal system of claim 1, wherein the solubilizer is a polar solvent.

4. The transdermal system of claim 1, wherein the solubilizer is selected from propylene glycol, ethylene glycol, glycerol, alkyl alcohol, N-methyl-pyrrolidone, formamide, acetamide, polyethylene glycol, and diethylene glycol monoethyl ether.

5. The transdermal system of claim 1, wherein the adhesive matrix comprises about 45-90 w/w % of the adhesive polymer.

6. The transdermal system of claim 5, wherein the adhesive polymer is selected from a polyisobutylene, an acrylic adhesive polymer, a polystyrene block copolymer, a butyl rubber, and a silicone rubber.

7. The transdermal system of claim 6, wherein the acrylic adhesive polymer is selected from a polyacrylic acid, a methacrylic acid, a polyacrylate, and a polymethacrylate.

8. The transdermal system of claim 1, wherein the adhesive matrix layer comprises about 5-20 w/w % memantine salt.

9. The transdermal system of claim 1, further comprising a contact adhesive layer in direct or indirect contact with the adhesive matrix, the contact adhesive layer comprising a contact layer adhesive polymer and a contact layer solubilizer, and a contact layer memantine salt soluble in the contact layer solubilizer to at least about 10 mg/mL at 25° C.

10. A method of transdermally administering memantine to a subject in need thereof, comprising: providing a transdermal drug delivery system according to claim 1.

* * * * *